United States Patent [19]

Ikenaka et al.

[11] Patent Number: 5,120,644
[45] Date of Patent: Jun. 9, 1992

[54] PEPTIDE DERIVATIVES AND ACTIVITY MEASURING METHOD OF PHYSIOLOGICALLY ACTIVE SUBSTANCES USING THE SAME AS SUBSTRATES

[75] Inventors: Tokuji Ikenaka, Sakai; Tomohiro Mega, Yao; Yasuki Hamazume, Obama, all of Japan

[73] Assignee: Wako Pure Chemical Industries, Ltd., Osaka, Japan

[21] Appl. No.: 256,078

[22] Filed: Oct. 6, 1988

Related U.S. Application Data

[63] Continuation-in-part of Ser. No. 32,253, Mar. 31, 1987, abandoned.

[30] Foreign Application Priority Data

Apr. 1, 1986 [JP] Japan ................. 61-76349

[51] Int. Cl.$^5$ .................. C12Q 1/37; C12Q 1/48; C12Q 1/42
[52] U.S. Cl. ........................ 435/15; 435/4; 435/21; 435/23; 435/24; 530/802
[58] Field of Search ............ 435/4, 15, 21, 23, 24; 530/802

[56] References Cited

U.S. PATENT DOCUMENTS

| | | | |
|---|---|---|---|
| 4,251,628 | 2/1981 | Ryan et al. | 435/24 |
| 4,275,153 | 6/1981 | Gargiulo et al. | 435/13 |
| 4,314,936 | 2/1982 | Yaron et al. | 260/112.5 R |
| 4,327,178 | 4/1982 | Ryan et al. | 435/23 |
| 4,409,140 | 10/1983 | Smith et al. | 260/112.5 R |
| 4,474,691 | 10/1983 | Schindler et al. | 260/112.5 R |
| 4,505,852 | 3/1985 | Rasnick | 260/112.5 |
| 4,507,389 | 3/1985 | Weingarten | 435/23 |
| 4,557,862 | 12/1985 | Mangel | 260/112.5 |
| 4,812,409 | 3/1989 | Babb et al. | 435/7 |

FOREIGN PATENT DOCUMENTS

| | | |
|---|---|---|
| 0084941 | 8/1983 | European Pat. Off. |
| 0192393 | 8/1986 | European Pat. Off. |
| 784181 | 10/1957 | United Kingdom |

OTHER PUBLICATIONS

Chemical Abstracts, vol. 100, No. 23, Jun. 4, 1984, p. 619, abstract No. 192235h, Columbus, Ohio, US; B. Wysocka-Skrzela: "Research on tumor inhibiting compounds. Part LXVII. Synthesis of peptide and phosphonamino acid derivatives of 1-nitroacridine", & Pol. J. Chem. 1982, 56(10-12) 1573.

Chemical Abstracts, vol. 101, No. 19, Nov. 5, 1984, p. 743, abstract No. 171702p, Columbus, Ohio, US; V. A. Shibnev et al.: "2-Methoxy-6,9-dichloroacridine in peptide synthesis as a fluorescent label", & Bioorg. Khim. 1984, 10 (5), 610-617.

Chemical Abstracts, vol. 101, No. 19, Nov. 5, 1984, pp. 746-747, abstract No. 171738e, Columbus, Ohio, US; V. A. Shibnev et al.: "Attachment of a fluorescent 2-methoxy-6-chloroacridine group to peptides", & Bioorg. Khim. 1984. 1984, 10(7), 921-926.

Journal of Medicinal Chemistry, vol. 19, No. 12, 1976, pp. 1422-1423; R. M. Peck et al.: "Carcinogenicity of derivatives of polynuclear compounds"* p. 1423, table I*.

J. Biochem. 98, 1293-1299 (1985).
Biochem. 15, 1958 (1976).
J. Am. Chem. Soc. 95, 1310-1315 (1973).
Kemp, B. E. et al., *Proc. Nat. Acad. Sci. USA*, vol. 73, No. 4, pp. 1038-1042 (Apr. 1976).

*Primary Examiner*—Esther L. Kepplinger
*Assistant Examiner*—Toni R. Scheiner
*Attorney, Agent, or Firm*—Armstrong, Nikaido, Marmelstein, Kubovcik & Murray

[57] ABSTRACT

Activities of physiologically active substances such as endopeptidases, proteases, transferases, phosphatases, protein kinase and the like enzymes can be measured specifically with high sensitivity by using as a substrate a peptide derivative having 2 to 15 amino acid units and a group which can emit fluoresence and/or absorb ultraviolet light as at least one terminal group.

7 Claims, 2 Drawing Sheets

PEPTIDE DERIVATIVES AND ACTIVITY MEASURING METHOD OF PHYSIOLOGICALLY ACTIVE SUBSTANCES USING THE SAME AS SUBSTRATES

This application is a continuation-in-part of application Ser. No. 032,253 filed on Mar. 31, 1987, now abandoned.

BACKGROUND OF THE INVENTION

This invention relates to peptide derivatives and processes for measuring activities of physiologically active substances by using the same as substrates Substances composed mainly of amino acids such as peptide hormones, enzymes, and the like fulfill various important physiological functions in living bodies. When these physiological functions appear, it is known that there take place in living bodies specific modifications of peptides such as, cleavages of peptide bonds, addition of sugars, phosphoric acid groups, sulfonic acid groups, sulfuric acid groups, etc. to peptides, and also specific elimination reactions of some groups. For example, there are concretely known activation of polypeptide hormones by limited proteolysis, controls of biological activities of proteins by phosphorylation, cleavage of the leader peptide, addition or elimination of sugar chains to proteins, etc. Elucidation of these modifications is medically and physiologically very important. Various studies have therefore been carried out as to physiologically active substances causing such reactions.

In activity measurements of physiologically active substances acting on peptides, proteins, etc., it is most in general to measure the changes of the substrates by various actions due to the physiologically active substances such as modification, elimination, and decomposition using peptides or proteins as substrates. For example, in the case of measuring protease or peptidase activities, synthesized substrates introduced a chromogenic group into peptides or amino acids are used. As the chromogenic group, there can be used coumarin, naphthylamine, nitroaniline, hippuric acid, and derivatives of these compounds. The activity can be determined by measuring fluorescence intensity or a change of absorbance (absorption curve) of the chromogenic group liberated by hydrolysis of the bond between the chromogenic group and the amino acid, or by measuring absorbance of a coloring matter obtained by a color producing reaction of the liberated chromogenic group and a coupler. As mentioned above, the method comprising hydrolyzing the bond directly by the physiologically active substance and measuring the liberated chromogenic group is simple and easy. But since the portion which is hydrolyzed is the bond between the amino acid and the chromogenic group, such a method is not suitable for measuring a physiologically active substance high in specificity. Further, the application of this method is limited in number since the method can not applied for the physiologically active substances which do not accompany with peptide cleavage. Moreover, according to a process wherein a peptide portion of a substrate is hydrolyzed by the aimed physiologically active substance, and the chromogenic group is liberated further by coupled exopeptidase, etc., the influence of contaminated other physiologically active substances is interferenced since the hydrolyzed substance is not measured directly On the other hand, there is disclosed in Journal of Biochemistry 98, 1293–1299 (1985) a process wherein a peptide is used as a substrate, an amino group produced by hydrolysis is reacted with fluorescamine, and the fluorescence produced is measured. This method is good in sensitivity, but has defects in that the aimed amino group cannot be determined correctly, when other portions of the peptide are hydrolyzed by contaminated other physiologically active substances. In such a case, there is a fear of providing a large error since the measured value include the extra amino groups. Further, according to the above-mentioned reference, it is disclosed that it is possible to specify and to determine quantitatively the hydrolyzed portion by separation and determination of the reaction products using a high performance liquid chromatography. But since the absorption of peptide bond at near 220 nm is measured, there are defects in that the sensitivity is low and that many contaminants often interfere the UV-absorption.

As methods for measuring enzymes which have functions for addition or elimination of specified functional groups (e.g. phosphoric acid groups, sulfonic acid groups, sulfuric acid groups, acyl groups, etc.), there are only reported methods for using radioisotopes as disclosed, for example in Biochemistry 15, 1958–1967 (1976). According to the article of the above-mentioned Biochemistry, by using a protein such as histone, casein, or the like and adenosine 3-phosphate labelled with an isotope $^{32}P$, an enzyme which phosphorilates a protein is measured. This process is high in sensitivity, but there are defects in that it cannot be determined which portion of the protein is phosphorylated and a special devices and a careful handling are necessary due to the use of radioisotope.

SUMMARY OF THE INVENTION

It is an object of this invention to provide a peptide derivative suitable as a substrate for measuring an activity of a physiologically active substance overcoming the defects of the prior art.

It is another object of this invention to provide a process for measuring an activity of a physiologically active substance acting on peptides, proteins, and the like easily and specifically with high sensitivity.

This invention provides a peptide derivative having 2 to 15 amino acid units and represented by the formula:

$$R^1\text{-}A^1\text{-}A\text{-}A^2\text{-}R^2 \quad (I),$$

or $$R^1\text{-}A^1\text{-}A^2\text{-}R^2 \quad (II)$$

wherein A is an amino acid residue or a peptide residue having 2 to 13 amino acid units; $A^1$ is an amino acid residue wherein the terminal N atom is bonded to a substituent $R^1$; $A^2$ is an amino acid residue wherein the terminal C atom is bonded to a substituent $R^2$; $R^1$ is a group which can emit fluorescence by combining with a —NH— group and/or absorb ultraviolet light, hydrogen or an amino protective group; and $R^2$ is a hydroxyl group, a carboxyl protective group, or a group of the formula:

$$-\text{NH}-Y-R^3$$

in which Y is a straight- or branched-alkylene chain group having 1 to 10 carbon atoms or a phenylene group; and $R^3$ is a fluorescence-emitting and/or ultraviolet absorbing group; provided that when $R^1$ is hydrogen or an amino protective group, $R^2$ is —NH—Y—$R^3$, and when $R^2$ is a hydroxyl group or a carboxyl protective group, $R^1$ is a group which can emit fluorescence by combining with a —NH— group and/or absorb ultraviolet light.

This invention also provides a process for measuring an activity of a physiologically active substance, which comprises reacting the physiologically active substance with a substrate which is a peptide derivative having 2 to 15 amino acid units and represented by the formla (I) or (II), and separating a reaction product produced by the action of the physiologically active substance, and measuring the quantity thereof.

BRIEF DESCRIPTION OF THE DRAWINGS

FIGS. 1(a) and 1(b) show charts of high performance liquid chromatography obtained in Example 6, in which

FIG. 3(a) and 3(b) show charts of high performance liquid chromatography obtained in Example 8, in which

FIG. 5 is a graph showing relationship between the renin concentration and the peak area obtained in Example 10.

DESCRIPTION OF THE PREFERRED EMBODIMENTS

The peptide derivative used as the substrate and having 2 to 15 amino acid units is represented by the formula:

$$R^1-A^1-A-A^2-R^2 \quad \text{(I)ps}$$

or $$R^1-A^1-A^2-R^2 \quad \text{(II)}$$

In the formula (I) or (II), $R^1$ is hydrogen, an amino protective group, or a group which can emit fluorescence by combining with a —NH— group and/or absorb ultraviolet light such as a 2-pyridyl group, a 3-pyridyl group, a phenyl group, or a substituted phenyl group. As the substituent group in the substituted phenyl group, there can be used a lower alkyl group having 1 to 6 carbon atoms such as a methyl group, an ethyl group, a propyl group, a butyl group, etc., a lower alkoxy group having 1 to 4 carbon atoms such as a methoxy group, an ethoxy group, a propoxy group, etc., a hydroxyl group, a carboxyl group, a sulfonic acid group, a halogen atom such as chlorine, bromine, or iodine. As the amino protective group, there can be used conventionally used ones such as a carbobenzoxy group, a succinyl group, an alkoxycarbonyl group having 2 to 18 carbon atoms, etc.

In the formula (I) or (II), $R^2$ is a hydroxyl group, a carboxyl protective group, or a group of the formula: —NH—Y—$R^3$. As the carboxyl protective group, there can be used conventionally used ones such as an aralkyloxy group, e.g. a benzyloxy group, a phenethyloxy group, etc. In the formula: —NH—Y—$R^3$, $R^3$ is a fluorescence-emitting and/or ultraviolet absorbing group such as a 2-pyridyl group, a 3-pyridyl group, an anilino group, a substituted anilino group wherein the substituent group is a lower alkyl group having 1 to 6 carbon atoms such as a methyl group, an ethyl group, a propyl group, a butyl group, etc., a lower alkoxy group having 1 to 4 carbon atoms such as a methoxy group, an ethoxy group, a propoxy group, etc., a hydroxyl group, a carboxyl group, a sulfonic acid group, a halogen atom such as chlorine, bromine, iodine, etc.; and Y is a straight- or branched-alkylene chain group having 1 to 10 carbon atoms, or a phenylene group.

In the formula (I) or (II), when $R^1$ is hydrogen or an amino protective group, $R^2$ should be —NH—Y—$R^3$, and when $R^2$ is a hydroxyl group or a carboxyl protective group, $R^1$ should be a group which can emit fluorescence and/or absorb ultraviolet light such as a 2-pyridyl group, a 3-pyridyl group, a phenyl group or a substituted phenyl group.

In the formula (I), A is an amino acid residue or a peptide residue having 2 to 13 amino acid units. Examples of the amino acid residues are as follows:

| Amino acid residue | Abbreviation |
|---|---|
| Alanyl | Ala |
| Arginyl | Arg |
| Asparaginyl | Asn |
| Aspartyl | Asp |
| Cysteinyl | Cys |
| Cystyl |  <br> Cys   Cys |
| Glutaminyl | Gln |
| Glutamyl | Glu |
| Glycyl | Gly |
| Histidyl | His |
| Hydroxylysyl | Hyl |
| Hydroxyprolyl | Hyp |
| Isoleucyl | Ile |
| Leucyl | Leu |
| Lysyl | Lys |
| Methionyl | Met |
| Phenylalanyl | Phe |
| Prolyl | Pro |
| Seryl | Ser |
| Threonyl | Thr |
| Tryptophanyl | Trp |
| Tyrosyl | Tyr |
| Valyl | Val |

In the formula (I) and (II), $A^1$ is an amino acid residue wherein the terminal N atom is bonded to the substituent $R^1$, and $A^2$ is an amino acid residue wherein the terminal C atom is bonded to the substituent $R^2$. There is no particular limit to the amino acid residues, which can be selected depending on an object to be measured.

The peptide derivative of the formula (I) or (II) should have a group which can emit fluorescence and/or absorb an ultraviolet light in the form of, for example, a 2-pyridyl amino group, a 3-pyridyl amino group, etc.; a group which can absorb an ultraviolet light such as an anilino group, a substituted anilino group, a phenyl group, or a substituted phenyl group at either the terminal N atom side or the terminal C atom side of the peptide, or both. When one of these groups exists only at the terminal N atom side or the terminal C atom side of said peptide, another end of the peptide may be a non-modified amino acid unit.

When there is a fear that the substrate is hydrolyzed by the action of exopeptidase contaminated in a sample, the terminal amino acid unit may be modified. As the modifying agent, there can be used those which can reduce the action of exopeptidase contaminated in the sample. Examples of such modifying agents are amino protective groups conventionally used and carboxyl protective groups conventionally used.

Amino acids such as $\beta$-, $\gamma$-, $\delta$-amino acids and the like, for example, $\beta$-alanine, $\beta$-aminobutyric acid, $\gamma$-aminobutyric acid, $\delta$-amino-n-valeric acid, etc. can be used as either $A^1$, $A^2$ or $R^1$ or $R^2$, since these amino acids have both functions as amino acid units and modifying agents.

Further, when $A^1$ is derived from an N-substituted amino acid such as N-methylamino acid, it is not necessary to further modify such an amino acid N-terminal group.

The peptide chain can be synthesized by a conventional method such as a step method, a fragment method, a solid phase method, a liquid phase method, or the like. The introduction of terminal groups can be carried out by a conventional method The peptide derivatives of the formula (I) and (II) can be synthesized, for example, as follows.

Introduction of a pyridylamino group into the N-terminal amino acid can be carried out according to a process described in Bull, Chem. Soc. Japan, 33, 1392–1394 (1960). That is, after refluxing an aqueous solution of formaldehyde and sodium bisulfite for several tens minutes to several hours, 2-aminopyridine is added thereto, followed by about 1 hour's reflux. Subsequently, sodium cyanide is added thereto and the reaction is continued at about 90° C. for several hours. After the reaction, the reaction solution is filtered and the filtrate is extracted with chloroform or the like. The extract is concentrated under reduced pressure and crystals of 2-pyridylaminoacetonitrile are obtained, followed by washing with ether. The thus obtained 2-pyridylaminoacetonitrile is hydrolyzed with hydrochloric acid and concentrated under reduced pressure and the crystals of 2-pyridylglycine.hydrochloride are obtained.

The synthesis of peptide bond reaction from the 2-pyridylglycine.hydrochloride and glycine can be carried out, for example, as follows: To N-2-pyridylglycine, are added dichloromethane, N,N'-dicyclohexylcarbodiimide and glycine ethyl ester. After stirring at room temperature for several hours, the reaction solution is filtered. The filtrate is purified by using, for example, high performance liquid chromatography to give Pyr-Gly-Gly-OEt.

Introduction of a pyridylamino group into the C-terminal amino acid can be carried, for example, as follows. 2-Chloropyridine and ethylenediamine are refluxed for several hours on an oil bath. After cooling, the solution is concentrated under reduced pressure, followed by addition of hydrochloric acid and methanol to crystallize N-(2-pyridyl)ethanediamine.hydrochloride, which is then separated. Then, dimethylformamide, triethylamine and carbobenzoxyalanyl-p-nitrophenyl ester are added and stirred at room temperature for 10 to 30 hours. After filtering, the filtrate is purified using, for example, high performance liquid chromatography to give Z—Ala—NH—CH$_2$CH$_2$—NH—Pyr.

The peptide derivatives of the formula (I) or (II) have high solubility in water and excellent stability, so that it can be used as a substrate for determining activities of physiologically active substances, which show various actions such as addition, elimination, decomposition, etc. for peptides and proteins, with specificity and high sensitivity.

That is, by using the peptide derivatives of the formula (I) or (II) as a substrate for a physiologically active substance having action for peptides and proteins, a product produced by the action of the physiologically active substance can be separated and measured to determine the activity of the physiologically active substance effectively.

Examples of the physiologically active substances having actions for peptides and proteins are endopeptidases or endoproteases such as elastase, trypsin, serine proteases, acid proteases, thiol protease, and metalloendopeptidases, which hydrolyze peptide bonds; transferases which conduct transfer action to peptides or amino acids; protein kinases which conduct phosphorylation of seryl, tyrosyl, or threonyl residue in a peptide, or protein such as casein kinase, protein kinase A, protein kinase C, and tyrosine kinase; protein phosphatases which conduct elimination of phosphoric acid groups contained in proteins or peptides; enzymes which add sugar chains to asparaginyl residues in proteins or peptides; glycosyltransferases or glucohydrolases which act on sugar chains to elongate or split the chains; other enzymes which conduct addition or removal of a sulfonic acid group, a sulfuric acid group, a methyl group, an acyl group, or the like for proteins or peptides; and the like.

Using the substrates of this invention, various physiologically active substances can be measured as follows:

(i) Measurement of Endoproteases and Elastase Substrates (1) Pyr-Gly(or Ala)-Gly-Glu-Lys-Lys-Leu↓Leu↓Lys-Phe-Glu-$\beta$-Ala Pyr=2-pyridyl or 3-pyridyl The mark ↓ in the amino acid sequences means cleavage portion by elastase That is, when elastase acts on the above mentioned substrate, the peptide is splitted at the portion indicated by the mark ↓ to produce newly two kinds of peptides having the pyridylamino group at a terminal. Thus, these two peptides are separated to measure the elastase activity.

(ii) Measurement of Protein Kinases Substrates (1) Pyr—Gly(or Ala)—Glu—Asp—Glu—Tyr—Ala—Ala—Arg—Arg—NH—(CH$_2$)$_2$—NH—Pyr (2) Pyr—Gly(or Ala)—Arg—Lys—Glu—Ser—Thr—Ser—Val—NH—(CH$_2$)$_2$—NH—Pyr (3) Pyr—Gly(or Ala)—Arg—Lys—Arg—Ser—Arg—Lys—NH—(CH$_2$)$_2$—NH-Pyr (4) Pyr—Gly(or Ala)—Arg—Lys—Asp—Thr—Pro—Ala—Leu—NH—(CH$_2$)$_2$—NH—Pyr (5) Pyr—Gly(or Ala)—Arg—Lys—Val—Ser—Ser—Ala—Glu—NH—(CH$_2$)$_2$—NH—Pyr (6) Pyr—Gly(or Ala)—Gly—Pro—Arg—Thr—Thr—Arg—Ala—Gln—NH—(CH$_2$)$_2$—NH—Pyr (7) Pyr—Gly(or Ala)—Gly—Glu—Ser—Ser—Glu—Glu—Asp—$\beta$—Ala (8) Pyr—Gly(or Ala)—Gly—Asp—Arg—Val—Tyr—Ile—His—Pro—NH—(CH$_2$)$_2$—NH—Pyr (9) Pyr—Gly(or Ala)—Arg—Lys—Ala—Ser—Gly—Pro—NH—(CH$_2$)$_2$—NH—Pyr
(10) Pyr—Gly(or Ala)—Ser—Gly—Ser—Phe—Lys—Leu—NH—(CH$_2$)$_2$—NH—Pyr
(11) Pyr—Gly(or Ala)—Arg—(or Lys)—Lys—Ser—Pro—Lys—NH—(CH$_2$)$_2$—NH—Pyr
(12) N—Acetyl—Ser—Gly—Arg—Gly—NH—(CH$_2$)$_2$—NH—Pyr
(13) Pyr—Gly(or Ala)—Thr—Arg—Ser—Ser—Arg—Ala
(14) Pyr—Gly(or Ala)—Lys—Lys—Gly—Ser—Lys—Ala (15) Pyr——Gly(or Ala)——Pro——Ala—⁠Ac⁠—Lys——*Ser——Ala——Pro——Lys—⁠Ac⁠—Lys

(16) N—acetyl—Ser—Gly—Arg—Gly—Lys—NH—(CH$_2$)$_2$—NH—Pyr
(17) Pyr—Gly(or Ala)—Lys(or Arg)—Gln—Ile—Ser—Val(or Ile)—Arg—Gly—NH—(CH$_2$)$_2$—NH—Pyr
(18) Pyr—Gly(or Ala)—Arg(or Lys)—Glu—Ile—Ser—Val—Arg—NH—(CH$_2$)$_2$—NH—Pyr
(19) Pyr—Gly(or Ala)—Arg—His—Gly—Ser—Lys—Tyr—Leu—NH—(CH$_2$)$_2$—NH—Pyr
(20) Pyr—Gly—Arg—Gly—Leu—Ser—Leu—Ser—Arg—NH—(CH$_2$)$_2$—NH—Pyr
(21) Pyr—Gly(or Ala)—Arg—Gly—Ser—Gly—Lys—Asp—Gly—NH—(CH$_2$)$_2$—NH—Pyr
(22) Pyr—Gly(or Ala)—Arg—Leu—Ser—Ile—Ser—Thr—Glu—NH—(CH$_2$)$_2$—NH—Pyr
(23) Pyr—Gly(or Ala)—Gln—Ser—Gly—Ser—Val(or Ile)—Try—Pro—NH—(CH$_2$)$_2$—NH—Pyr
(24) Pyr—Gly(or Ala)—Arg—Ala—Ile—Thr—Ala—Arg—Arg—NH—(CH$_2$)$_2$—NH—Pyr
(25) Pyr—Gly(or Ala)—Val—Lys—Ser—Ser—Lys—Glu—NH—(CH$_2$)$_2$—NH—Pyr
(26) Pyr—Gly(or Ala)—Val—Arg—Met—Ser—Ala—Asx—NH—(CH$_2$)$_2$—NH—Pyr
(27) Pyr—Gly(or Ala)—Leu—Arg—Arg—Ala—Ser—Leu—Arg—NH—(CH$_2$)$_2$—NH—Pyr
(28) Pyr—Gly(or Ala)—(Arg)—Arg—Ser—Ser—Ser—Arg—(Pro)—NH—(CH$_2$)$_2$—NH—Pyr
(29) Pyr—Gly(or Ala)—(Arg)—Val—Ser—Arg—(Arg)—NH—(CH$_2$)$_2$—NH—Pyr
(30) Pyr—Gly(or Ala)—(Arg)—Ala—Ser—Arg—(Arg)—NH—(CH$_2$)$_2$—NH—Pyr
(31) Pyr—Gly(or Ala)—(Arg)—Arg—Ser—Ser—Arg—(Arg)—NH—(CH$_2$)$_2$—NH—Pyr The mark * in an amino acid sequence means a portion to which a phosphoric acid group is added by a protein kinase. That is, when a protein kinase acts on the above-mentioned substrate, a phosphoric acid group is added to the portion marked with * to produce a compound different from the substrate. Thus, the compound is separated to measure the protein kinase activity.

(iii) Measurement of Protein Phosphatases

All the substrates mentioned in above (ii) and attaching phosphoric acid groups at the portions marked with * can be used as substrates for protein phosphatases. The protein phosphatases are enzymes which function quite reverse to the protein kinases and eliminate the phosphoric acid groups contained in proteins or peptides. Thus, the peptides having phosphoric acid groups serve as substrates, and the peptides obtained by releasing the phosphoric acid groups are products obtained by the action of physiologically active substances.

(iv) Measurement of Renin or Angiotensin Converting Enzyme (ACE-I) Substrates

The mark ↓ in the amino acid sequences means cleavage portions by each enzyme. That is, when each enzyme acts on the above-mentioned substrates, the peptides are splitted to produce two kinds of peptides newly. Thus, these products are separated to measure the activity of each enzyme.

(v) Measurement of Various Hormone Regulating Enzymes (V-1) Measurement of Post-proline Cleaving Enzyme Substrates (1) Pyr—Gly(or Ala)—Arg—Pro—Pro↓Gly—Phe—Ser—NH—(CH$_2$)$_2$—NH—Pyr (hydrolysis of bradykinin)

(2) Pyr—Gly(or Ala)—Arg—Pro↓Gly—NH—(CH$_2$)$_2$—NH—Pyr (hydrolysis of LH—RH)

(3) Cys—Tyr—Ile—Gln—Asn—Cys—Pro—Leu—Gly—NH—(CH$_2$)$_2$—NH—Pyr (hydrolysis of oxytocin)

(V-2) Measurement of Pyroglutamate Peptidase Substrates (1) Pyroglutamic acid↓Gly—Pro—NH—(CH$_2$)$_2$—NH—Pyr (2) Pyroglutamic acid↓Gly—Lys—NH—(CH$_2$)$_2$—NH—Pyr (3) Pyroglutamic acid↓His—Pro—NH—(CH$_2$)$_2$—NH—Pyr (4) Pyroglutamic acid↓His—Trp—NH—(CH$_2$)$_2$—NH—Pyr (V-3) Measurement of Other Enzymes Substrates (1) Pyr—Gly(or Ala)—Arg—Pro—Lys—Pro—Gln—Gln↓Phe↓Phe—Gly↓Leu—Met—NH—(CH$_2$)$_2$—NH—Pyr (substance P)

(2) Pyr—Gly(or Ala)—Glu—Glu—Glu—Ala—#Tyr—Gly—Trp—NH—(CH$_2$)$_2$—Pyr (gastrin)

(3) # Pyr—Gly(or Ala)—Asp—Arg—Asp—#Tyr—Met—Gly—Trp—NH—(CH$_2$)$_2$—NH—Pyr (cholecrystokinin)

The mark ↓ in the amino acid sequences means cleavage portions by the enzymes to be measured and the mark # means portions to which sulfonic acid groups are added by the enzymes to be measured. In the former, the peptides or amino acids newly formed by the cleavage are separated, and in the latter the peptides to which sulfonic acid groups are attached are separated, to measure the enzymatic activities, respectively.

The activity of physiologically active substances can be measured under the following conditions. The reaction temperature is not particularly limited but is preferably about 20° to 40° C. The reaction time is properly selected depending on purposes. pH of the reaction is properly selected depending on purposes. As a buffer to maintain the reaction pH properly; there can be used a phosphate buffer, a tris-hydroxymethylamine-HCl buffer, a glycine-NaOH buffer, a Good's buffer, an acetate buffer, or the like.

Substances produced by the action of the physiologically active substances such as addition-elimination reaction, hydrolysis reaction, transfer action, etc., can be separated and measured as follows. In the case of separating the products depending on the degree of change of hydrophilic properties or hydrophobic properties, there can be used ordinary phase or reversed phase chromatography. When the molecular weight changes largely, there can be used gel filtration chromatography. When the modification of ionic groups or demodification takes place, there can be used ion exchange chromatography. When the sugar chain is added or released or the special peptide structure changes, there can be used the principle of affinity chromatography, etc. Particularly when the high performance liquid chromatography (HPLC) is used for the separation and the measurement, the results can remarkably advantageously be obtained in a very short time.

One example of conditions for the high performance liquid chromatography is as follows. It is preferable to use a chemically bonded type silica gel introducing an octadecylsilane, octylsilane, amino, phenyl, trimethylsilane or the like group thereinto. As the eluent, there can preferably be used acetonitrile, 1-buthanol, methanol, and other solvent added with an ammonium acetate buffer solution, trifluoroacetate buffer solution or other buffer solution and having a pH of 2.0 to 6.0, either isocratic or gradient type. Needless to say, the eluent is not limited thereto. The flow rate can be selected freely depending on column sizes and separation capacity, but be preferably 0.5 to 2.0 ml/min.

The quantitative determination (or detection) is generally conducted by a fluorescence method or a ultraviolet method conventionally used. For example, the -pyridylamino group introduced into the peptide derivative for use in the detection is suitable for both emitting fluorescence and absorbing an ultraviolet light. These compounds are usually measured by using a wavelength of 300 to 330 nm of exciting light and a wavelength of 350 to 410 nm of fluorescent light in the case of using fluorescent light, and a wavelength of 300 to 310 nm in the case of using ultraviolet light.

According to this invention, the activity of physiologically active substances acting on peptides, proteins, etc. can be measured with specificity and extremely high sensitivity (a reaction product can be detected in several picomoles), and further with high selectivity for the aimed reaction.

The physiologically active substances to be measured according to this invention are naturally present in living bodies, so that it is very possible that various substances are co-existing at the time of measurement. When such co-existing substances do not influence the measurement of the physiologically active substances, there is no special problem. But since the peptide derivatives are used as substrates for the measurement in this invention, when enzymes such as endoproteases, endopeptidases, protein phosphatases, elastase, and the like (hereinafter referred to as "interfering enzymes") are co-existing, the measurement is inevitably influenced by these interfering enzymes. But according to this invention, since the various peptide derivatives can be synthesized, the problem can be solved by synthesyzing the peptide derivatives by properly selecting amino acids which constitute the peptides and hardly be acted by the interfering enzymes. But, sometimes, there may be difficult to use such peptide derivatives containing amino acids suitable for such conditions depending on substances to be measured. In such a case, the use of an inhibitor for the interfering enzymes will solve such a problem. As the inhibitors, there can be used those which do not inhibit the enzymatic activity of an enzyme to be measured but act effectively on the co-existing interfering enzymes. Examples of such inhibitors are pepstatin, phosphoramidon, leupeptin, antipain, chymostatin, elastatinal, diisopropyl fluorophosphate (DFP), N-tosyl-L-phenylalanine chloromethyl ketone (TPCK), N-α-p-tosyl-L-lysine chloromethyl ketone (TLCK), antibodies for enzyme proteins, soybean trypsin inhibitor, kalikrein inhibitor, α2-macroglobulin, etc. for proteases; bestatin, amastatin, etc., for peptidases; forphenicine, etc., for phosphatases; and esterastin for esterases.

This invention is illustrated by way of the following Examples, wherein the following abbreviations are used:

| | |
|---|---|
| Pyr = pyridyl | Ser = seryl |
| Gly = glycyl | Asp = aspartyl |
| Ala = alanyl | Leu = leucyl |
| Glu = glutamyl | Gln = glutaminyl |
| Lys = lysyl | Phe = phenylalanyl |
| Boc = t-butoxycarbonyl | Bzl = benzyl |
| Cl-Z = Chlorinated carbobenzoxy | TBA = t-butylamine |
| DCC = N,N'-dicyclohexylcarbodiimide | |
| DCHA = dicyclohexylamine | |

EXAMPLE 1

Synthesis of 2-pyridylglycine

A 37% formaldehyde solution in an amount of 8.2 g was added to an aqueous solution of sodium bisulfite in an amount of 10.8 g/16 ml H$_2$O and refluxed for 30 minutes. Then, 9.4 g of 2-aminopyridine was added thereto and refluxed for another 1 hour. Then, an aqueous solution of 25 sodium cyanide in an amount of 10 g/50 ml H$_2$O was added thereto to carry out the reaction at 90° C. for 4 hours with stirring. The reaction solution was filtered and the filtrate was extracted with about 50 ml of chloroform 6 times. After drying over sodium sulfate, the chloroform layer was concentrated to crystallize. The crystals were filtered and washed with ether (yield, about 7.2 g). After recrystallization from chloroform, there was obtained 2-pyridylaminoacetonitrile in an amount of 5.9 g (yield 44%). Hydrolysis of the 2-pyridylaminoacetonitrile was carried out in 100 ml of 6N HCl for 3 hours with refluxing, followed by concentration for crystallization. The crystals were filtered, washed with ether and recrystallized from water to give 7.5 g of 2-pyridylglycine.hydrochloride (yield 90.1%).

$^1$H-NMR (100 MHz, D$_2$O): δ 4.3 (s, 2H, —CH$_2$—), 6.8–7.0 (m, 2H, pyridine H), 7.7–8.0 ppm (m, 2H, pyridine H).

| Elementary analysis [hydrochloride] (as C$_7$H$_9$O$_2$N$_2$Cl) | | | | |
|---|---|---|---|---|
| | C(%) | H(%) | N(%) | Cl(%) |
| Found | 44.40 | 4.83 | 14.70 | 18.56 |
| Calcd. | 44.58 | 4.81 | 14.85 | 18.80 |

UV maximum absorption wavelength: $\lambda_{max}$=238, 310 nm
Excitation wavelength: Ex.$_{max}$=318 nm
Emission maximum wavelength: Em.$_{max}$=360 nm

EXAMPLE 2

Synthesis of 2-pyridyl DL-alanine

To an aqueous solution of sodium bisulfite in an amount of 10.5 g/20 ml H$_2$O, a 44% acetaldehyde solution in an amount of 10 g was added and refluxed with heating for 1 hour. Then, 9.4 g of 2-aminopyridine was added thereto and the reflux with heating was continued for additional 2 hours. Aqueous solution of sodium cyanide was added thereto in an amount of 7 g/10 ml H$_2$O and reacted at 90° C. for 2 hours. The oil layer was separated and cooled to be crystallized (yield 11.6 g). The crystals were recrystallized from ethyl acetate to give α-(2-pyridylamino)propionitrile in an amount of 9 g (in 67% yield).

After hydrolyzing 3 g of the α-(2-pyridylamino)propionitrile in 50 ml of 6N HCl for 5 hours with refluxing, the reaction solution was concentrated while removing deposited crystals (NH$_4$Cl). The concentrated solution was adsorbed on an ion exchange resin [adsorbent: Dowex 50 H$^+$, column: 1.6×12 cm]. After washing well with water, the substance was eluted with a 0.2 M ammonium acetate solution, and yellow fractions were collected and concentrated to dryness. In order to remove the ammonium acetate, water is added thereto, and subjected to concentration to dryness again. After adding concentrated hydrochloric acid thereto, recrystallization was conducted from water to give about 2 g of crystals of 2-pyridyl DL-alanine.hydrochloride which is a precursor of the substrate of this invention (yield 60%).

$^1$H-NMR (100 MHz, D$_2$O): δ1.44, 1.52 (d, 3H, —CH$_3$), 4.0–4.2

(q, 1H, —CH—), 6.8–7.0 (m, 2H, pyridine H), 7.7–8.0 ppm (m, 2H, pyridine H).

| Elementary analysis [hydrochloride] (as C$_8$H$_{11}$O$_2$N$_2$Cl) | | | | |
|---|---|---|---|---|
| | C(%) | H(%) | N(%) | Cl(%) |
| Found | 47.29 | 5.46 | 13.69 | 17.48 |
| Calcd. | 47.42 | 5.47 | 13.83 | 17.50 |

UV maximum absorption wavelength: $\lambda_{max}$=238, 310 nm
Excitation wavelength: Ex.$_{max}$=290 nm
Emission maximum wavelength: Em.$_{max}$=370 nm

EXAMPLE 3

Synthesis of Pyr-Gly-Gly-OEt

To 9.4 mg (50 μmol) of 2-pyridylglycine.hydrochloride, 1 ml of dichloromethane, 50 μmol of DCC, and in an amount of 70 μmol/200 μl CHCl$_3$ were added and reacted at room temperature for 3 hours. The color of the reaction solution was changed from yellow to dark blue. After filtering the reaction solution, the desired product was dispersed by reverse phase high performance liquid chromatography (HPLC) in yield of 38%.

HPLC [column: filler ODS - 120T (a trade name, manufactured by Toyo Soda Manufacturing Co., Ltd.), 7×250 mm); eluent 25% CH$_3$CN— 0.01M NH$_4$OAc (pH 5.6); flow rate 3 ml/min.]
Elution time: 6.2 min.

$^1$H-NMR (100 MHz, CDCl$_3$): δ1.20–1.34 (t, 3H, —CH$_3$), 2.9 (broad s, 1H, 4.0-4.3 (m, 6H, —CH₂—), 5.25 (broad s, 6.4-6.8 (m, 2H, pyridine H), 7.4-7.6 ppm (m, 2H, pyridine H).

EXAMPLE 4

Synthesis of Leu—NH—CH₂CH₂—NH—Pyr

A mixture of 12 g (10 ml) of 2-chloropyridine and 100 ml of ethylenediamine was refluxed for 5 hours and then unreacted ethylenediamine was distilled off under reduced pressure. After dissolving the residue in 1N NaOH, the resulting solution was extracted with chloroform several times. The chloroform layer was concentrated. Hydrochloric acid was added thereto form a hydrochloride, followed by addition of methanol for crystallization to yield 11 g of N-(2-pyridyl)-1,2-ethanediamine.hydrochloride (in 91% yield).

¹H-NMR (100 MHz, D₂O): δ3.4-3.5 (t, 2H, —CH₂—CH₂—NH—Pyr), 3.8-3.9 (t, 2H, NH₂—CH₂—CH₂—), 7.0-7.3 (m, 2H, pyridine H), 7.9-8.2 ppm (m, 2H, pyridine H).

Then, to 250 mg of Boc-LeuOH.H₂O, benzene was added. After removing the water of crystallization by an evaporator, the residue was dissolved in 5 ml of chloroform, followed by addition of 206 mg of DCC with stirring. After 20 minutes, a chloroform solution of the previously synthesized N-(2-pyridyl)ethanediamine in an amount of 206 mg/5 ml was added thereto, followed by reaction overnight. After filtering the reaction solution to remove a precipitate, the solvent was removed by distillation. The residue was dissolved in chloroform and washed with a 2.5% Na₂CO₃ aqueous solution and water in this order. The chloroform layer was dryed over magnesium sulfate and concentrated to give Boc—Leu—NH—CH₂CH₂—NH—Pyr.

To this, 0.1 ml of anisole and 0.5 ml of trifluoroacetic acid (TFA) were added under cooling and reacted at 0° C. for 2 hours to split off the Boc group. After adding ether, unsolved substances were collected and dried well in a desiccator containing KOH therein to give Leu—NH—CH₂CH₂—NH—Pyr which is a precursor of the substrate of this invention (in about 70% yield).

¹H-NMR (100 MHz, D₂O): δ0.85 (2, 6H, —C(CH₃)₂), 1.4-1.6 (m, 3H, 3.3-3.6 (m, 4H, —NH—CH₂—CH₂—NH—Pyr), 3.8-4.0

6.7-7.0 (m, 2H, pyridine H), 7.6-7.9 ppm (m, 2H, pyridine H).

EXAMPLE 5

Synthesis of Pyr-Gly-Glu-Lys-Lys-Leu-Leu-Lys-Phe-Glu-β-Ala

The synthesis was conducted according to a solid phase method described in J. Am. Chem. Soc., 95, 1310-1315 (1973).

That is, using 1 g of chloromethyl polystyrene resin [divinylbenzene 2%, 100-200 mesh, Cl: 0.93 mmol/g] (mfd. by Wako Pure Chemical Industries, Ltd.) ½ equivalent weight of Boc-β-alanine was introduced according to a conventional method, and then the Boc group was eliminated by TFA. Then, each 3-fold equivalent weight of Boc-amino acid was introduced according to a DCC method in the following order: Boc-Glu (OBz 1), Boc-Phe.DCHA, Boc-Lys(Cl-Z).TBA, Boc-Leu.H₂O, Boc-Leu.H₂O, Boc-Lys(Cl-Z). TBA, Boc-Lys(Cl-Z). TBA, Boc-Glu(OBZL), and Pyr-Gly obtained in Example 1. In the above-mentioned Boc-Phe DCHA and Boc-Glu, the coupling reaction was conducted twice. After cutting of the peptide from the resin by HF treatment and splitting of Bzl, Z and individual protective groups, Pyr-Gly-Glu-Lys-Lys-Leu-Leu-Lys-Phe-Glu-β-Ala was obtained by gel filtration using Toyo Pearl HW 40 (a trade name, mfd. by Toyo Soda Manufacturing Co., Ltd.). This product was purified by using a high performance liquid chromatography (yield 55%).

By means of a mass apectrum of the compound after the HF treatment, it was admitted that the peak of the molecular weight was well agreed to the calculated value of 1329.

Amino acid analyzed values: Glu 2.1, Leu 2.0, Phe 1.0, Lys 3.0 and β-Ala 1.2.

EXAMPLE 6

Measurement of elastase using Pyr-Gly-Glu-Lys-Lys-Leu-Leu-Lys-Phe-Glu-β-Ala as substrate Preparation of Reagent Solutions ① Substrate solution A substrate solution was prepared by dissolving 1.2 mg of Pyr-Gly-Glu-Lys-Lys-Leu-Leu-Lys-Phe-Glu-β-Ala produced in Example 5 in 50 ml of 0.01 M tris-hydroxymethylaminomethane-HCl buffer solution (pH 8.0).

② Enzyme solution

An enzyme solution was prepared by dissolving 3.6 mg of elastase (derived from pig pancreas, mfd. by Sigma Chemical Co.) in 100 μl of 0.01 M tris-hydroxymethylaminomethane-HCl buffer solution (pH 8.0).

Measuring Method

To 200 μl of the substrate solution, 5 μl of the enzyme solution was added and allowed to stand at 37° C. in a constant temperature bath.

After 20, 40, 60, 120 and 180 minutes, 10 μl of the reaction solution was taken out at each time and analyzed by using a high performance liquid chromatography.

Analytical Conditions

Column: octadecylsilyl group-bonded reverse phase type, DDS-120 T (mfd. by Toyo Soda Manufacturing Co., Ltd.), 4×150 mm Eluting conditions:

A liquid: A 6% acetonitrile aqueous solution containing 0.05% trifluoroacetic acid B liquid: A 24% acetonitrile aqueous solution containing 0.05% trifluoroacetic acid Linear gradient of the A liquid and the B liquid was conducted at a flow rate of 1 ml/min from 0 minute to 15 minutes.

Detection:

| Fluorescent light: | Excitation wavelength | 310 nm |
|---|---|---|
| | Emission wavelength | 370 nm |

Results of Measurement

Figure 1A:
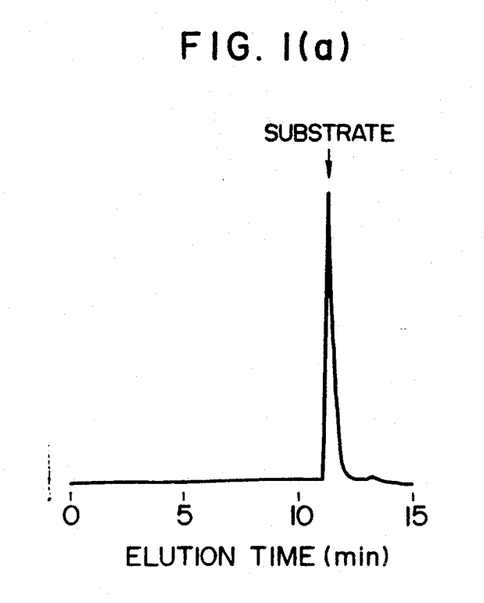
FIG. 1(a) is a chart of blank and FIG. 1(b) is a chart after 2 hours from the beginning of the reaction.
Figure 1B:
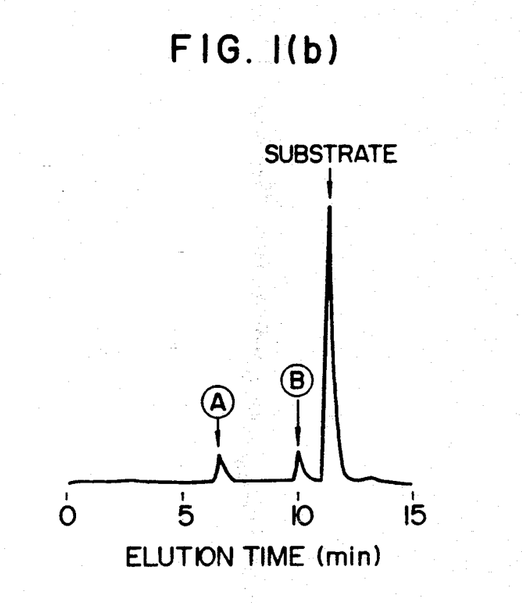

FIG. 1 shows the results measured by using a high performance liquid chromatography. FIG. 1(a) shows a chart of blank and FIG. 1(b) shows a chart after 2 hours from the beginning of the reaction.

As is clear from FIG. 1, two peaks (A) and (B) are produced by the reaction. From the results of amino acid analysis, these peaks are identified as (A)=Pyr-Gly-Glu-Lys-Lys-Leu and (B)=Pyr-Gly-Glu-Lys-Lys-Leu-Leu. Therefore, it is revealed that elasterase hydrolyzes the substrate at two portions.

Figure 2:
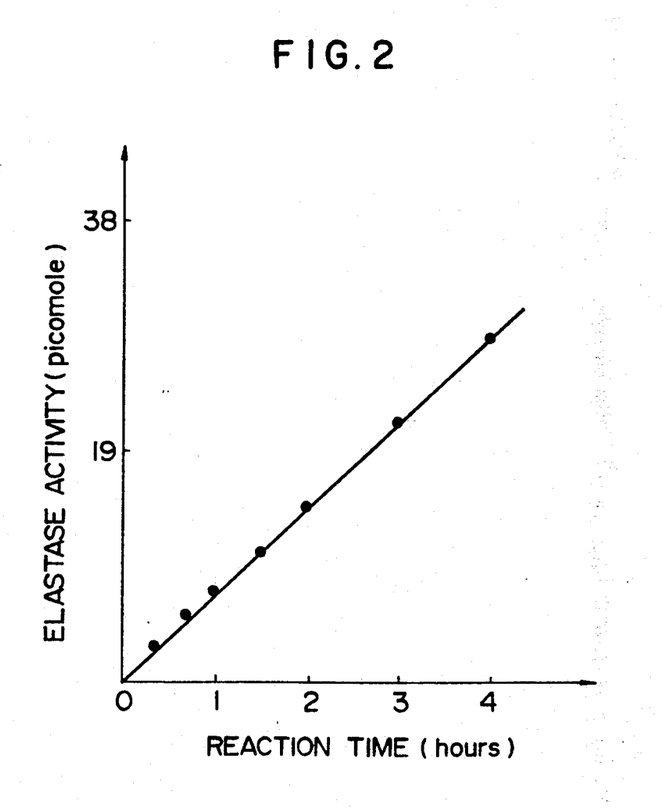
FIG. 2 is a graph showing a relationship between the elastase activity and the time elapsed.

Further, by quantitatively determining (A), the time course was linear at the range of 40 picomole or less. This time course is shown in FIG. 2.

EXAMPLE 7

Synthesis of Pyr-Gly-Glu-Ser-Ser-Glu-Glu-Asp-$\beta$-Ala

The synthesis was conducted by the solid phase method disclosed in J. Am. Chem. Soc., 95, 1310–1315 (1973) in the same manner as in Example 5.

That is, using 1 g of chloromethyl polystyrene resin [divinylbenzene 2%, 100 to 200 mesh, Cl: 0.93 mmol/g, mfd. by Wako Pure Chemical Industries, Ltd.], ½ equivalent weight of Boc-$\beta$-alanine was introduced thereinto by a conventional method, followed by elimination of the Boc group by TFA. Then, 3-fold equivalent weights of Boc-amino acids were introduced by the DCC method in the following order: Boc-Asp (OBZL), BOC-Glu(OBZL), BOC-Glu(OBZL), BOC-Ser-(OBZL), BOC-Ser; (OBzl), Glu(OBZL), Gly(BOZL) and Pyr-Gly. Among them, coupling reaction was carried out two times in the case of Boc-Glu(OBZL). After splitting of the peptide from the resin by HF treatment and splitting of Bzl, Z and individual protective groups, Pyr-Gly-Glu-Ser-Ser-Glu-Glu-Asp-$\beta$-Ala was obtained by gel filtration using Toyo pearl HW 40 (a trade name, mfd. by Toyo Soda Manufacturing Co., Ltd.). This substance was purified by high performance liquid chromatography (yield 58%).

Analysis of amino acids: Glu 3.0, Ser 1.8, Asp 1.1 $\beta$-Ala 1.2

EXAMPLE 8

Measurement of Protein Kinase Activity by using Pyr-Gly-Glu-Ser-Ser-Glu-Glu-Asp-$\beta$-Ala as Substrate

[Preparation of Reagent Solutions]

① Buffer solution

A buffer solution was prepared by dissolving in 80 ml of water 272 mg of imidazole, 142 mg of magnesium chloride, 1.1 g of potassium chloride, 76 mg of glycol ether diamine-N,N,N',N'-tetraacetic acid and 12 mg of adenosine-3-phosphoric acid, adding HCl to make the pH 7.5 and making the total amount 100 ml.

② Substrate solution

A substrate solution was prepared by dissolving 2.7 mg of Pyr-Gly-Glu-Ser-Ser-Glu-Glu-Asp-$\beta$-Ala in 3 ml of water.

③ Sample

A sample was prepared by dissolving purified protein kinase obtained from human red blood cells in a proper amount in the buffer solution according to Boivin et al: B.B.R.C. vol. 89 (1), 7–16 (1979). The resulting sample was further diluted by using the buffer solution to the proportions of ¼, 2/4, ¾ and 4/4.

Measuring Method

After adding 10 μl of the substrate solution to 20 μl of the buffer solution, each 10 μl of sample was added thereto and reacted at 30° C. for 1 hour. Then, each 4 μl was sampled and subjected to the analysis by high performance liquid chromatography.

Analytical Conditions

Column: filler, a reverse phase type containing bonded octadecylsylyl group, ODS, S-5 mfd. by Yamamura Kagaku K.K., 4×150 mm Eluting conditions:

eluent: an aqueous solution of 0.05% trifluoroacetic acid containing 10% acetonitrile flow rate: 1.0 ml/min Detection:

| Fluorescent light: | Excitation wavelength | 320 nm |
|---|---|---|
| | Emission wavelength | 410 nm |

Measurement Results

Figure 3A:
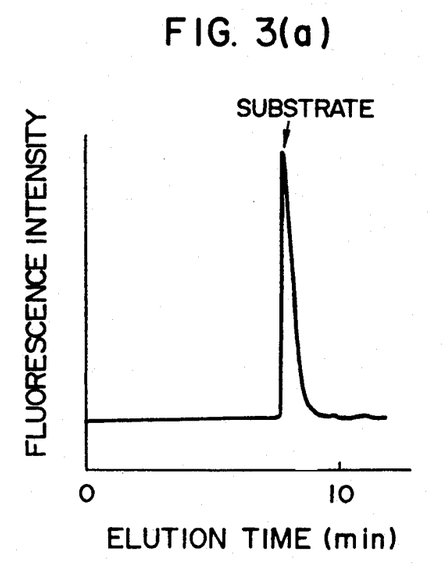
FIG. 3(a) is a chart of blank and FIG. 3(b) is chart using the ½ diluted sample.
Figure 3B:
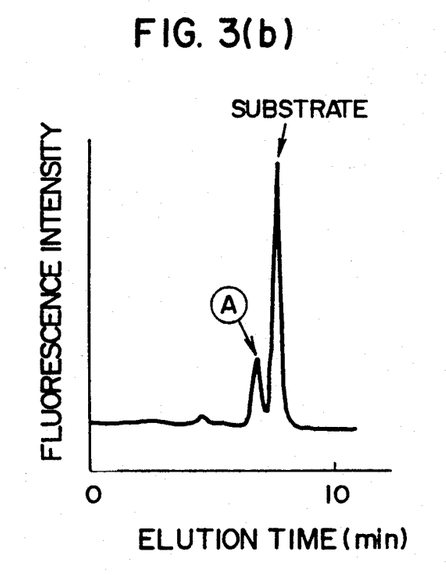
Figure 4:
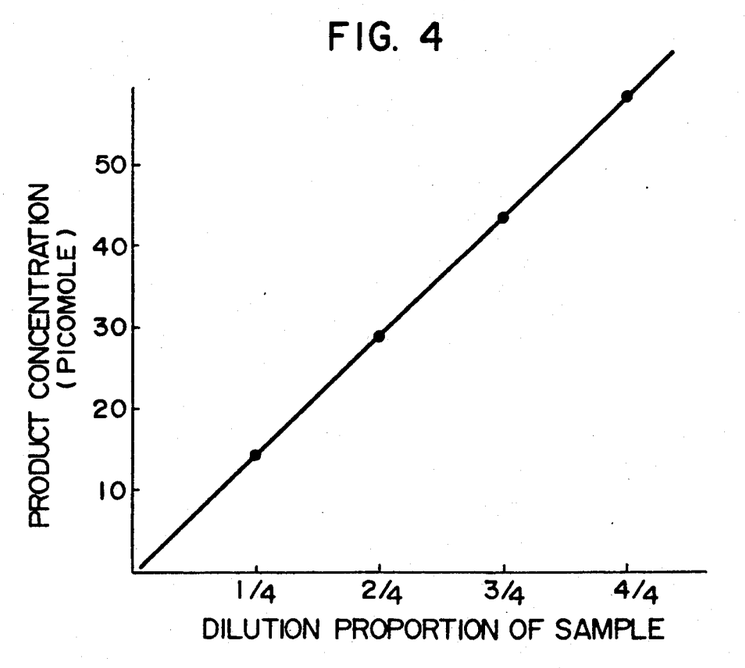
FIG. 4 is a graph showing a relationship between the product concentration and the dilution proportion of the sample used in Example 8.

FIGS. 3(a) and 3(b) show the results measured by using high performance liquid chromatography. FIG. 3(a) shows a chart of blank and FIG. 3(b) shows a chart using the ¼ diluted sample. As is clear from FIG. 3, one peak (A) is produced by the reaction. The quantitative analysis of phosphorus revealed that the peak (A) is produced by the phosphorus oxidation of the substrate. The produced peak (A) (product concentration) was measured with regard to the dilution proportion of the samples. The results are shown in FIG. 4. As is clear from Fig. 4, there is obtained a linear relationship.

As mentioned above, when the peptide derivative of the formula (I) or (II) is use as a substrate for measuring activity of a physiologically active substance, the activity of the physiologically active substance acting on peptides, proteins, etc. can be measured with specificity and extremely high sensitivity (the reaction product can be detected in the order of several picomoles) and further with selecting reacting portions of the physiologically active substance.

EXAMPLE 9

Synthesis of Pyr-Pro-Phe-His-Leu-Leu-Val-Tyr-$\beta$-Ala

The synthesis was conducted according to a solid phase method described in J. Am. Chem. Soc., 95, 1310–1315 (1973).

That is, using 1 g of chloromethyl poly-styrene resin [divinylbenzene 2%, 100–200 mesh, Cl: 0.93 mmol/g (mfd. by Wako Pure Chemical Industries, Ltd.)] ½ equivalent weight of BOC-$\beta$-alanine was introduced according to a conventional method, and then the BOC group was eliminated by TFA. Then each 3-fold equivalent weight of BOC-amino acid was introduced according to a DCC method in the following order: BOC-Tyr (O-Bz), BOC-Val, BOC-Leu, BOC-Leu, BOC-His (TOS), BOC-Phe, BOC-Pro, and Pyr-Gly obtained in Example 1. In the above-mentioned, the coupling reaction as conducted twice. After cutting of the peptide form the resin by HF treatment and splitting of BZL, TOS and individual protective groups, Pyr-Pro-Phe-His-Leu-Leu-Val-Tyr-$\beta$-Ala obtained by gel filtration using Toyo Pearl HW 40 (a trade name, mfd. by Toyo Soda Manufacturing Co. Ltd.). This product was purified.

Amino acid analyzed values: Tyr 0.92, Val 1.08, Leu 2.0, His 0.89, Phe 0.91, Pro 1.01, $\beta$-Ala 1.02

EXAMPLE 10

Measurement of Renin Activity Using Pyr-Pro-Phe-His-Leu-Leu-Val-Tyr-$\beta$-Ala as a Substrate.

Preparation of Reagent Solutions

1 Substract Solution

A substrate solution was prepared by dissolving 1.6 mg of Pyr-Pro-Phe-His-Leu-Leu-Val-Tyr-$\beta$Ala produced in Example 9 in 25 ml of 0.10 M tris-hydroxymethylaminomethane-MES buffer solution (pH 6.0)

2 Enzyme Solution

An enzyme solution was prepared by dissolving 0.3 mg of renin (derived from pig kidney, mfd. by Sigma Chemical Co.) in 300 $\mu$l of 0.01 M tris-hydroxymethylaminomethane-MES buffer solution (pH 6.0). This solution was diluted with same buffer to appropriate concentrations.

Measuring Method

To 30 $\mu$l of the substrate solution, 10 $\mu$l of the enzyme solution was added and allowed to stand at 37° C. in a constant temperature bath. After 30 minutes, 50 $\mu$l of acetic acid was added and analyzed by using a high performance liquid chromatography.

Analytical Conditions

Column: octadecasilyl group-bonded reverse phase type Wakosil 5C$_{18}$ (mf. by Wako Pure Chemical Ind., Ltd.) 4.6×150 mm.

Eluting conditions:

A liquid: A 10% acetonitrile aqueous solution containing 0.10% trifluoroacetic acid B liquid: A 60% acetonitrile aqueous solution containing 0.10% trifluoroacetic acid B liquid was conducted at a flow rate of 1.5 ml/min from 5 minutes to 35 minutes. Detection:

Fluorescent light: Excitation wavelength 320 nm Emission wavelength 400 nm

Results of Measurement

By quantitatively determining a peak that was produced by the reaction, a linear relationship between renin concentration and the peak area was observed (FIG. 5).

What is claimed is:

1. A process for measuring the activity of an enzyme, which comprises reacting the enzyme with a substrate which is a peptide derivative having 2 to 15 amino acid units represented by formula I or formula II:

wherein A is an amino acid residue or a peptide residue having 2 to 13 amino acid units; $A^1$ is an amino acid residue wherein the N-terminal is bonded to substituent $R^1$; $A^2$ is an amino acid residue wherein the C-terminal is bonded to substituent $R^2$; $R^1$ is a substituent selected from the group consisting of hydrogen, an amino protective group, a group which fluoresces when combined with an —NH— group; and $R^2$ is a substituent selected from the group consisting of hydroxyl, an aralkyloxy carboxyl protective group, and groups of formula III:

wherein Y is straight—or— branched-chain $C_1$-$C_{10}$ alkylene, or phenylene; and $R^3$ is a substituent selected from the group consisting of 2-pyridylamino, 3-pyridylamino, which may be substituted with at least one $C_{1-6}$ alkyl, $C_{1-4}$ alkoxy, sulfonyl, and halo group and can emit fluorescence; with the provisos that:

(a) when $R^1$ is hydrogen or an amino protective group, $R^2$ is —NH—Y—$R^3$, and (b) when $R^2$ is hydroxyl or an aralkyloxy carboxyl protective group, $R^1$ is not hydrogen or an amino protective group; separating a fluorescent amino acid or a fluorescent peptide produced by the action of the enzyme, and measuring the amount of reaction product.

2. A process according to Claim 1, wherein the separating and measuring are conducted by using a high performance liquid chromatograph.

3. A process according to Claim 1, wherein the physiologically active substance is an endopeptidase or an endoprotease which hydrolyzes peptide bonds, a transferase which conducts a transfer reaction of peptides or amino acids, a protein phosphatase which conducts elimination of phosphoric acid groups contained in proteins or peptides, an enzyme which adds sugar chains to asparaginyl residues in proteins or peptides, an enzyme which acts on sugar chains added to proteins or peptides to elongate or split the sugar chains, or an enzyme which conducts addition or removal of a sulfonic acid group, a sulfuric acid group, a methyl group, or an acyl group for proteins or peptides.

4. A process according to Claim 1, wherein the physiologically active substance is elastase.

5. A process according to Claim 1, wherein the physiologically active substance is protein kinase.

6. A process according to claim 1, wherein said peptide derivative is selected from the group consisting of 2-pyridyl-Gly-Gly-OEt, 3-pyridyl-Gly-Gly-OEt, 2-pyridyl-Gly-Glu-Lys-Lys-Leu-Leu-Lys-Glu-$\beta$-Ala, 3-pyridyl-Gly-Glu-Lys-Lys-Leu-Leu-Lys-Glu-$\beta$-Ala, 2-pyridyl-Gly-Gly-Glu-Ser-Ser-Glu-Glu-Asp-$\beta$-Ala and 3-pyridyl-Gly-Gly-Glu-Ser-Ser-Glu-Glu-Asp-$\beta$-Ala.

7. A process according to claim 1, wherein $R^3$ is selected from the group consisting of 2-pyridylamino and 3-pyridylamino.

* * * * *